United States Patent [19]

Bonaventura

[11] Patent Number: 5,773,417
[45] Date of Patent: Jun. 30, 1998

[54] HUMAN SERUM ALBUMIN-PORPHYRIN COMPLEXES WITH THE ABILITY TO BIND OXYGEN AND THERAPEUTIC USES THEREOF

[75] Inventor: Joseph Bonaventura, Beaufort, N.C.

[73] Assignee: Duke University, Durham, N.C.

[21] Appl. No.: 906,828

[22] Filed: Aug. 6, 1997

Related U.S. Application Data

[63] Continuation of Ser. No. 279,371, Jul. 22, 1994, abandoned.
[51] Int. Cl.$^6$ .......................... A61K 38/00; A61K 35/16; C07K 1/00
[52] U.S. Cl. ............................... 514/21; 514/6; 514/185; 514/322; 530/302; 530/363; 530/385; 530/830; 424/529; 424/530; 424/531
[58] Field of Search ................................. 514/21, 6, 185, 514/322; 530/362, 363, 385, 830; 424/529, 4, 530, 531

[56] References Cited

U.S. PATENT DOCUMENTS

| 5,296,466 | 3/1994 | Kilbourn et al. ........................... 514/6 |
| 5,334,705 | 8/1994 | Bonaventura et al. ................. 530/385 |
| 5,349,054 | 9/1994 | Bonaventura et al. .................. 530/385 |
| 5,480,866 | 1/1996 | Bonaventura et al. ..................... 514/6 |
| 5,629,198 | 5/1997 | Mizumoto et al. ..................... 435/262 |

FOREIGN PATENT DOCUMENTS

| 0 066 884 A2 | 12/1982 | European Pat. Off. . |
| 0 601 183 A1 | 6/1994 | European Pat. Off. . |
| 55-144048 | 11/1980 | Japan . |
| 58-10514 | 1/1983 | Japan . |
| 58-213711 | 12/1983 | Japan . |
| 3-128321 | 5/1991 | Japan . |
| WO 93/03035 | 2/1993 | WIPO . |
| WO 93 03426 | 2/1993 | WIPO . |
| WO 93 03035 | 2/1994 | WIPO . |
| WO 94 15628 | 7/1994 | WIPO . |

OTHER PUBLICATIONS

Bonaventura et al., 1994, "Oxygen–binding albumins: A novel approach to blood substitutes,", *Artif. Cells Blood Substitutes Immobilization Biotechnol.* 22(5):Abstract A83.
Komatsu et al., 1995, "$O_2$–Transport Albumin: A New Hybrid–Haemoprotein Incorporating Tetraphenylporphyrinatoiron(II) Derivative," *Chem. Lett.* 9:813–814.
Collman et al., 1994, "Congruent Multiple Michael Addition for the Synthesis of Biomimetic Heme Analogues," *J. Am. Chem. Soc.* 116: 2681–2682.
Lee and Hirose, 1992, "Partially Folded State of the Disulfide–reduced Form of Human Serum Albumin as an Intermediate for Reversible Denaturation," *J. Biol. Chem.* 267: 14753–14758.
Bonkovsky et al., 1991, "Intravenous Heme–Albumin in Acute Intermittent Porphyrin: Evidence for Repletion of Hepatic Hemoproteins and Regulatory Heme Pools," *Am. J. Gastroenterol.* 86: 1050–1056.

Carter and He, 1990, "Structure of Human Serum Albumin," *Science* 249: 302–303.
Davila and Harriman, 1990, "Photochemical and Radiolytic Oxidation of a Zinc Porphyrin Bound to Human Serum Albumin," *J. Am. Chem. Soc.* 112: 2686–2690.
Carter et al., 1989, "Three–Dimensional Structure of Human Serum Albumin," *Science* 244: 1195–1198.
Datta–Gupta et al., 1989, "Binding Studies of Four Free Base Porphyrins and Six Iron (+3) Porphyrins with Human Serum Albumin," *Res. Comm. Chem. Pathol Pharmacol.* 63: 289–292.
Datta–Gupta et al., 1988, "Binding Studies of Three Water–Soluble Polycationic Porphyrins with Human Serum Albumin," *Res. Comm. Chem. Pathol. Pharmacol.* 60: 347–360.
Imai and Kyuno, 1988, "Thermodynamics for Base Binding to Four Atropisomers of Cobalt(II) Picket Fence Porphyrin. Intramolecular Ligand–Ligand Interactions," *Inorgan. Chim. Acta* 153: 175–182.
Styer, 1988, "Oxygen–transporting Proteins: Myoglobin and Hemoglobin," Chapter 7 Biochemistry (W.H. Freeman and Co., New York), pp. 143–173.
Sharma et al., 1987, "Reaction in Nitric Oxide with Heme Proteins and Model Compounds of Hemoglobin," *Biochem.* 26: 3837–3843.
Tsuchida, 1987, "Macromolecule–Metal Complexes—Dynamic Separation of Molecular Oxygen through Macromolecule–Metal Complex Membranes," *UDC* 51: 13–26. (English Abstract).
Imai et al., 1986, "Effects of Polarity on Dioxygen Binding to Cobalt(II) Porphyrins," *Inorgan. Chim. Acta* 125: 151–158.
Uemori et al., 1986, "Cooperative Dioxygen Binding to the Bi–bridged Dimeric Porphyrinatocobolt(II) Complexes," *Inorgan. Chim. Acta.* 124: 153–160.
Vorobei et al., 1986, "Search for Photosensitive Agents Specifically Binding with Serum Albumin," *Biofizika* 31: 757–759. (English Abstract).
Bajdor et al., 1984, "Resonance Raman Studies of $O_2$ Stretching Vibrations in Oxygen Adducts of Cobalt Porphyrins. The Importance of Vibrational Coupling," *J. Am. Chem. Soc.* 106: 7741–7747.

(List continued on next page.)

*Primary Examiner*—Cecilia J. Tsang
*Assistant Examiner*—Abdel A. Mohamed
*Attorney, Agent, or Firm*—Pennie & Edmonds LLP

[57] ABSTRACT

The invention is directed to human serum albumin-porphyrin (HSA-P) complexes which are capable of reversible oxygen binding and their uses. These complexes may be used in applications requiring physiological oxygen carriers such as in blood substitute solutions, or in applications requiring plasma expanders. Methods for the production of these complexes are provided. In a specific example, HSA-P complexes are shown to exhibit reversible oxygen binding. In another example, the HSA-P complex does not exhibit appreciable vasoactivity.

42 Claims, 9 Drawing Sheets

OTHER PUBLICATIONS

Chu and Williams, 1984, "Kinetic Studies on the Reduction of Iron(III)Deuteroporphyrin–Human Serum Albumin Complex with Dithionite Ion," Arch. Biochem. Biophys. 294: 129–137.

Suslick et al., 1984, "Influence of CO and O2 to Iron(II) Porphyrins," J. Am. Chem. Soc. 106: 4522–4525.

Traylor et al., 1984, "Model Compound Studies Related to Peroxidases. Mechanisms of Reactions of Hemins with Peracids," J. Am. Chem. Soc. 106: 755–764.

Baldwin, 1983, "Recent Researches Towards Oxygen Carrying Chelates as Blood Substitutes," Advances in Blood Sub. Res., pp. 149–155.

Chu and Williams, 1983, "The Kinetic Studies on the Reduction of Iron(III)–Porphyrin–HSA Complexes," 74th Annual Meeting of the American Society of Biological Chemists, San Francisco, Calif., USA, Jun. 5–9, Fed. Proc. 42: 2071 (Absract No. 1837).

Herron et al., 1983, "Synthesis and Characterization of Some Reversible Iron(II) Dioxygen Carriers of Lacunar Macrobicyclic Ligands and Their Reactivities with Dioxygen," J. Am. Chem. Soc. 105: 6585–6596.

Imai et al., 1983, "Synthesis and Effectively Reversible Oxgenation of Some Picket Fence Type Porphyrinatocobalt(II) Complexes,"Synth. React. Inorg. Met.–Org. Chem 13: 761–780.

Moehring et al., 1983, "Heterogeneity of Albumin as Detected by its Interactions with Deuteroporphyrin IX," Biochemistry 22: 3381–3386.

Brown and Shockley, 1982, "Serum Albumin: Structure and Characterization of Its Ligand Binding Sites," *Ligand–Protein Interact*, (Wiley, New York, N.Y., Ed. Jost and Griffith) pp. 25–68.

Shigehara et al., 1981, "Oxygenation of Iron(II) Picket–Fence Porphyrin Bound to Amphiphilic Block Copolymer in Water," Macromol. 14:1153–1161.

Adams and Berman, 1980, "Kinetics and Mechanism of the Interaction Between Human Serum Albumin and Monomeric Haemin," Biochem. J. 191: 95–102.

Jameson et al., 1980, "Models for the Active Site of Oxygen–Binding Hemoproteins. Dioxygen Binding Properties and the Structures of (2–Methylimidazole)–meso–tetra–($\alpha$, $\alpha,\alpha,\alpha$–o–pivalamidophenyl)porphyrinatoiron(II)–Ethanol and its Dioxygen Adduct," J. Am. Chem. Soc. 102: 3224–3237.

Traylor et al., 1980, "Cyclophane Hemes. 3. Magnitudes of Distal Side Steric Effects in Hemes and Hemoproteins," J. Am. Chem. Soc. 102: 5939–5941.

Collier et al., 1979, "Studies on Haemin in Dimethyl Sulphoxide.Water Mixtures," Biochem. J. 179: 281–289.

Collman et al., 1979, "Carbon Monoxide Binding to Iron Porphyrins," Proc. Natl. Acad. Sci. 76: 6035–6039.

Janado et al., 1979, "Sodium Dodecyl Sulfate–Polyacrylamide Gel Electrophoresis of Bovine Serum Albumin Oligomers Produced by Lipid Peroxidation," J. Biochem. 86: 177–182.

Collman et al., 1978, "Model Compounds for the T State of Hemoglobin," Proc. Natl. Acad. Sci. 75: 564–568.

Collman et al., 1978, "Oxygen Binding to Cobalt Porphyrins," J. Am. Chem. Soc. 100: 2761–2766.

Hrkal et al., 1978, "Haeme Binding to Human Serum Albumin and to the Three Large Cyanogen Bromide Albumin Fragments," Int. J. Biochem. 9:349–355.

Chang and Traylor, 1975, "Kinetics of Oxygen and Carbon Monoxide Binding to Synthetic Analogs of the Myoglobin and Hemoglobin Active Sites," Proc. Natl. Acad. Soc. 72: 1166–1170.

Collman et al., 1975, "Oxygen Binding to Iron Porphyrins," J. Am. Chem. Soc. 97: 7185–7186.

Beaven et al., 1974, "A Spectroscopic Study of the Haemin–Human–Serum–Albumin System," Eur. J. Biochem. 41: 539–546.

Brinigar et al., 1974, "Solvent Effects on Reversible Formation and Oxidative Stability of Heme–Oxygen Complexes," J. Am. Chem. Soc. 96: 5597–5599.

Chang and Traylor, 1973, "Solution Behavior of a Synthetic Myoglobin Active Site," J. Am. Chem. Soc. 95: 5810–5811.

Chang and Traylor, 1973, "Proximal Base Influence on the Binding of Oxygen and Carbon Monoxide to Heme," J. Am. Chem. Soc. 95: 8477–8479.

Collman et al., 1973, "Reversible Oxygen Adduct Formation in Ferrous Complexes Derived from a Picket Fence Porphyrin. A Model for Oxymyoglobin, " J. Am. Chem. Soc. 95: 7868–7870.

Baur, 1969, "The Evolution of Methaemalbumin," Comp. Biochem. Physiol. 30: 657–664.

Van Nostrand Reinhold, 1984, *Encyclopedia Of Chemistry* 4th Ed., pp. 134–141.

Tuschida et al., 1983, "Water Soluble Polymer–Bound Iron–Porphyrins and Their Oxygen Binding Ability," *J. Pharm. Dyn.* 6:s–9.

Busch, D., 1982, "Chelate Compounds as Components of Acellular, Oxygen–Delivering, Resuscitation Fluids," *Critical Care Medicine*, 10(4):246–253.

Jones et al., 1979, "Synthetic Oxygen Carriers Related to Biological Systems" *Chemical Reviews* 79(2): 139–179.

Collman et al., 1976, "Nature of $O_2$ and CO binding to metalloporphyrins and heme proteins, " *Proc. Natl. Acad. Sci. USA* 73:(10): 3333–3337.

Honda et al., 1976, "Adsorption and Deposition of Molecular Oxygen in Solid State of Polymeric Hemochrome," *Bulletin of Chemical Society of Japan* 49(4):868–871.

Baldwin, J.E., 1975, "Chelating agents as possible artificial blood substitutes," *Artificial Blood Federation Proceedings* 34(6): 1441–1443.

Collman et al., 1973, "Syntheses of Ferrous–Porphyrin Complexes. A Hypothetical Model for Deoxymyoglobin," *Journal of the American Chemical Society* 95(6):2048–2049.

Kilbourn et al, *Biochem. Biophys. Res. Comm.*, vol. 199, pp. 155–162, 1994.

Cohen et al, *Biochem. J.*, vol. 270, pp. 325–330, 1990.

Tsuchida et al, *J. Chem. Soc., Dalton, Trans.*, vol. 6, pp. 1147–1151, 1984.

Dellacherie et al, *Crit. Rev. Ther. Drug Carriers*, vol. 3, pp. 41–94, 1986.

Collman et al, *Proc. Natl. Acad. Sci, USA*, vol. 75, pp. 1052–1055, 1978.

Collman et al, *J. Am. Chem. Soc.*, vol. 97, pp. 1427–1439, 1975.

Rodegro et al, *Chemical Abstracts*, vol. 98, p. 290, Ref. No. 103530a, 1983 (Photochem. Photobiol. 1983, 37(1), 99–103).

Takemura et al, *Chemical Abstracts*, vol. 116, p. 400, Ref. No. 123962m, 1992 (Photochem. Photobiol., 1992, 55(1), 137–140).

Kouratsu et al, *Chemistry Letters*, pp. 813–814, 1995.

Tie et al., 1995, "Peroxidatic activity of metalloporphyrin binding to serum albumin: enhancement effect of serum albumin on metalloporphyrin catalyzed luminol chemiluminescence reaction," *Analytica Chimica Acta* 300:215–220.

Sagawa et al., 1991, "Stereoselective Dioxygenolysis of a Tryptophan Derivative Catalyzed by a Maganese Porphyrin Bound to Bovine Serum Albumin," *Chemistry Letters* 2083–2086.

Kongshaug et al., 1989, "The distribution of porphyrins with different tumour localising ability amoung human plasma proteins," *Br. J. Cancer* 59:184–188.

Rotenberg et al., 1987, "Thermodynamics of Porphyrin Binding to Serum Albumin: Effects of Temperature, of Porphyrin Species and of Albumin–Carried Fatty Acids," *Photochemistry and Photobiology* 46(5):689–693.

Beltramini et al., 1987, "Steady–State and Time–Resolved Spectroscopic Studies on the Hematoporphyrin–Lipoprotein Complex," *Biochemistry* 26:6852–6858.

D. Kessel, 1986, "Porphyrin–Lipoprotein Associated as a Factor in Porphyrin Localization," *Cancer Letters* 33:183–188.

Rotenberg et al., 1985, "Deuteroporphyrin–albumin binding equilibrium," *Biochem. J.* 229:197–203.

Carter and Xo, 1994, "Structure of serum albumin," Advances in Protein Chemistry 45:153–203.

Kilbourn et al., 1994, "Cell–free hemoglobin reverses the endotoxin–mediated hyporesponsivity of rat aortic rings to β–adrenergic," Biochem. Biophys. Res. Comm. 199;155–162.

He and Carter, 1992, "Atomic structure and chemistry of human serum albumin," Nature 358:209–215.

Wuenschell et al., 1992, "H–bonded oxyhemoglobin models with substituted picket–fence porphyrins: The model compound equivalent of site–directed mutagenesis," J. Am. Chem. Soc. 114:3346–3355.

Cohen and Margalit, 1990, "Binding of porphyrin to human serum albumin," Biochem. J. 270:325–330.

Marden et al., 1989, "Flash photolysis of the serum albumin–heme–CO complex," Biochem. 28:4422–4426.

Bove, 1986, "Transfusion–transmitted diseases: current problems and challenges," Prog. in Hematol. XIV:123–147.

Dellacherie et al., 1986, "Synthetic carriers of oxygen," Crit. Rev. Ther. Drug Carriers 3:41–94.

Peters, 1985, "Serum albumin," Advances in Protein Chemistry 37:161–245.

Lexa et al., 1984, "Molecular environment effects in redox chemistry. Electrochemistry of ether–linked basket–handle and picket–fence iron porphyrins," J. Am. Chem. Soc. 106:4755–4765.

Tsuchida et al., 11984, "Liposomal heme as oxygen carrier under semi–physiological conditions," J. Chem. Soc. Dalton. Trans. 6:1147–1151.

Hawkins and Dugaiczyk, 1982, "The human serum albumin gene: structure of a unique locus," Gene 19:55–58.

Makino et al., 1982, "Spectral and carbon monoxide binding properties of Fe(II) picket–fence porphyrin and protoheme bound to liposomes," Biochem, Biophys. Res. Comm. 108:1010–1015.

Rose et al., 1982, "Carbon monoxide binding kinetics in capped porphyrin compounds," Proc. Natl. Acad. Sci. USA 79:5742–5745.

Traylor and Traylor, 1982, "Considerations for the design of useful synthetic oxygen carriers," Ann. Rev. Biophys. Bioeng. 11:105–127.

Sollenne et al., 1981, "Disruption of the tryptophan binding site in the human serum albumin dimer," Arch. Biochem. Biophys. 207:264–269.

Stryer, 1981, "Hemoglobin: An allosteric protein," Ch 4. from Biochemistry, published by W.H. Freeman and Company, New York, pp. 65–85.

Collman et al., 1978, "Cooperativity in $O_2$ binding to iron porphyrins," Proc. Natl. Acad. Sci. USA 75:1052–1055.

Almog et al., 1975, "Condensation of tetraaldehydes with pyrrole. Direct synthesis of Capped porphyrins," J. Am. Chem. Soc. 97:226–227.

Almog et al., 1975, "Reversible oxygenation and autoxidation of a capped porphyrin iron(II) complex," J. Am. Chem. Soc. 97:227–228.

Collman et al., 1975, "Picket fence porphyrins. Synthetic models for oxygen binding hemoproteins," J. Am. Chem. Soc. 97:1427–1439.

King and Spencer, 1970, "Structural studies and organic ligand–binding properties of bovine plasma albumin," J. Biol. Chem. 245:6134–6148.

Pederson and Foster, 1969, "Subtilsin cleavage of bovine plasma albumin. Reversible association of the two primary fragments and their relation to the structure of the parent protein," Biochemistry 8:2357–2365.

Markus et al., 1967, "Tryptic hydrolysis of human serum albumin," J. Biol. Chem. 242:4395–4401.

Andersson, 1966, "The heterogeneity of bovine serum albumin," Biochim. Biophys. Acta. 117:115–133.

Hughes and Dintzis, 1964, "Crystallization of the mercury dimers of human and bovine mercaptalbumin," J. Biol. Chem. 239:845–849.

Spahr and Edsell, 1964, "Amino acid composition of human and bovine serum mercaptalbumins," J. Biol. Chem. 239:850–854.

Hartley et al., 1962, "The relation of free sulfhydryl groups to chromatographic heterogeneity and polymerization of bovine plasma albumin," Biochemistry 1:60–68.

Williams and Foster, 1960, "The aggregation of bovine plasma albumin at low pH," J. Am. Chem. Soc. 82:3741–3745.

Riggs and Wolbach, 1956, "Sulfhydral groups and the structure of hemoglobin," J. Gen. Physiol. 39:585–605.

Straessle, 1954, "A disulfide dimer of human mercaptalbumin," J. Am. Chem. Soc. 76:3138–3142.

Cohn et al., 1946, "Preparation and properties of serum and plasma proteins. IV. A system for the separation into fractions of the protein and lipoprotein components of biological tissues and fluids," J. Am. Chem. Soc. 68:459–475.

HUMAN SERUM ALBUMIN-PORPHYRIN COMPLEXES WITH THE ABILITY TO BIND OXYGEN AND THERAPEUTIC USES THEREOF

This is a continuation of application Ser. No. 08/279,371, filed Jul. 22, 1994, now abandoned.

TABLE OF CONTENTS

1. INTRODUCTION
2. BACKGROUND OF THE INVENTION
   2.1 BLOOD SUBSTITUTES
   2.2 HUMAN SERUM ALBUMIN
   2.3 HEME
   2.4 ALBUMIN/PORPHYRINS
3. SUMMARY OF THE INVENTION
4. BRIEF DESCRIPTION OF THE FIGURES
5. DETAILED DESCRIPTION OF THE INVENTION
   5.1 Preparation of HSA-P
   5.2 Utilities of the Invention
6. EXAMPLE PREPARATION OF HUMAN SERUM ALBUMIN-PICKET FENCE PORPHYRINS
7. EXAMPLE: ABSORPTION SPECTRA OF OXYGEN BINDING BY THE HSA-PFP COMPLEX #1
8. EXAMPLE: OXYGEN-BINDING OF HSA-PFP #1
9. EXAMPLE: OXYGENATION CYCLES FOR HSA-PFP #2
10. EXAMPLE: VASOACTIVITY EXPERIMENT FOR HSA-PFP #1

INTRODUCTION

The present invention is directed to human serum albumin (HSA)-porphyrin complexes, and their production and uses. Human serum albumin-porphyrins (HSA-P) produced by methods of the present invention may be used in applications requiring physiological oxygen carriers such as in blood substitute solutions, or in applications requiring plasma expanders.

BACKGROUND OF THE INVENTION

2.1 BLOOD SUBSTITUTES

Treatment of many clinical conditions involving blood loss or blood deficiency requires supplementation with a source of donor blood or a blood substitute. A primary goal is to restore the circulation of oxygen through the body, a function that is physiologically mediated by the hemoglobin found in red blood cells.

Transfusion of a patient with donated blood, while used widely, has a number of disadvantages. Firstly, there may be a shortage of a patient's blood type. Secondly, transfused blood may be contaminated with infectious agents such as hepatitis viruses, cytomegaloviruses, Epstein-Barr virus, serum parvoviruses, syphilis, malaria, filariasis, trypanosomiasis, babsiosis, pathogenic bacteria, and HIV (Bove, Progr. Hematol. 14: 123-145, 1986). Thirdly, donated blood has a limited shelf life.

An alternative to transfused blood involves the use of blood substitutes. A blood substitute is an oxygen carrying solution that also provides the oncotic pressure necessary to maintain blood volume. Two types of blood substitutes have recently been studied, fluorocarbon emulsions and hemoglobin solutions.

Fluorocarbon emulsions, however, are not feasible blood substitutes, since they are known at times to block the immune system (Dellacherie, Crit. Rev. Ther. Drug Carriers 3:41-94, 1986). In addition, the use of fluorocarbons is limited to situations in which high partial pressures of oxygen can be administered. They do not have a sufficiently high oxygen binding capacity for use under normal physiological conditions.

Native isolated hemoglobin, when used as a blood substitute, has a number of disadvantages. Firstly, large dosages are required (Walder, Biotech '88, San Francisco, Nov. 14–16, 1988). A single unit (450 ml) of a 10% hemoglobin solution contains 45 g of protein. Since it is estimated that ten million units of blood are used in the U.S. per year, the production of 450,000 kg of hemoglobin would be required. Secondly, as cited previously, the potential exists for contamination of the isolated hemoglobin by any number of infectious agents. Thirdly, although hemoglobin is normally a tetramer of 64,000 molecular weight, it can dissociate to form alpha-beta dimers which are rapidly cleared by the kidneys, therefore lowering the effective residence time of functional hemoglobin in the body. Fourthly, cell-free hemoglobin has too high an oxygen affinity to effectively release oxygen to the tissues due to the absence of 2,3 diphosphoglycerate (2,3 DPG). Efforts to restore 2,3 DPG have been unsuccessful since 2,3 DPG is rapidly cleared from the circulation (Snyder and Walder, "Chemically Modified and Recombinant Hemoglobin Blood Substitutes" in Biotechnology of Blood, Butterworth-Heinemann, pages 101-116, 1991). Finally, cell-free hemoglobin has been shown to act as a scavenger of nitric oxide in the body, a property which results in a vasoconstrictive effect on blood vessels (Kilbourn, R., et al., Biochem. Biophys. Res. Comm. 199:155-162, 1994). This vasoactivity may compromise the utility of cell-free hemoglobin in certain clinical conditions.

2.2 HUMAN SERUM ALBUMIN

Human serum albumin, a protein of 585 amino acids with a molecular weight of 66,500 daltons, is the most abundant protein in human plasma. It comprises 60% of the total protein, with a normal concentration of 42 g/liter. It provides 80% of the osmotic pressure of blood, and is a very stable and soluble protein. It serves as a transport carrier for a variety of ligands, including fatty acids, amino acids, steroids, ions, and pharmaceuticals. It is able to shepherd hydrophobic ligands throughout the body. It was one of the first proteins to be crystallized, and the standard purification protocol was developed by Cohn in 1946 (Peters, "Serum Albumin", in Advances in Protein Chemistry, Academic Press, 1985).

The three-dimensional structure of human serum albumin was determined by X-ray crystallography to a resolution of 2.8 Å. Three homologous domains were identified and the principal ligand binding sites were localized (He and Carter, Nature 358:209-215, 1992; Carter and Ho, Adv. Protein Chem. 45:153-203, 1994).

2.3 HEM

Heme is a porphyrin in which a central iron atom is coordinately bound to the four pyrrole nitrogen atoms of the porphyrin ring. The physiological oxygen carriers, hemoglobin and myoglobin, contain a heme moiety that is the site of oxygen binding. Oxygen binds to the iron atom of free heme; however, only the ferrous (FeII) form of heme can bind oxygen. The binding of oxygen can rapidly lead to oxidation of the iron atom, creating ferric (FeIII) heme, which cannot bind oxygen. This oxidation reaction, therefore, has to be circumvented in order to optimize the capacity of the heme to reversibly bind oxygen for long periods. The three dimensional structure of the polypeptide moieties of myoglobin and hemoglobin result in a protective enclosure for the heme. This structure prevents the oxidation reaction which would occur upon the binding of oxygen by preventing the formation of an intermediate in this reaction, a sandwich dimer of two hemes with oxygen. Thus, the design of these molecules maximizes the oxygen binding capability of their heme moieties (Stryer, Biochemistry, Chapter 4, pp. 65–85, W. H. Freeman and Co., New York, 1981).

Efforts to modify hemes in order to design compounds which mimic the oxygen binding potential of the native heme in its hemoglobin or myoglobin pocket have resulted in the development of many porphyrin derivatives that have been tested for their ability to bind oxygen and exhibit resistance to oxidation (Traylor and Traylor, Ann. Rev. Biophys. Bioeng. 11:105-127, 1982). Such porphyrin derivatives include capped porphyrins (Almog et al., J. Am. Chem. Soc. 97:226-227, 1975; Rose et al., Proc. Natl. Acad. Sci. 79:5742-5745, 1982) and basket-handle porphyrins (Lexa et al., J. Am. Chem. Soc. 106:4755-4765, 1984)

Picket fence porphyrin is such a modified heme. It was designed as a model compound to mimic the oxygen binding site of myoglobin and hemoglobin. Four axial bases are covalently attached to the porphyrin ring, effectively creating a protective enclosure for bound oxygen due to the great steric bulk provided (Collman et al., Proc. Natl. Acad. Sci. 75:1052-1055, 1978). When oxygen binds to the iron atom, five of the six coordination positions of this molecule are then occupied. As a result, formation of the intermediate in the oxidation reaction is prevented by the steric design of the molecule, and oxidation is prevented. Efforts to optimize the picket-fence structure currently continue through the use of molecular modeling (Wuenschel et al., J. Am. Chem. Soc. 114:3346-3355, 1992).

Liposome-bound picket fence porphyrins were shown to bind CO with highs affinity, but were subject to autoxidation, and no stable oxygenated forms were observed (Makino et al., Biochem. and Biophys. Res. Comm. 108:1010-1015, 1982); these complexes were later shown to reversibly bind oxygen (Tsuchida et al., J. Chem. Soc. Dalton Trans., p. 1147-1151, 1984).

2.4 ALBUMIN/PORPHYRINS

Human serum albumin normally binds free heme in the body (heme-HSA); it acts as a scavenger for surplus heme released in hemorraghic conditions. The complex heme-HSA normally oxidizes to metheme-HSA. The resultant complex, methemalbumin, can be diagnostic for internal hemorrhage (Peters, supra).

Albumin, with its known affinity for porphyrins, has been studied to determine the effectiveness of this protein carrier for the delivery of hydroxyethyl vinyl deuteroporphyrin and irreversible porphyrin aggregates in photodynamic therapy of tumors (Cohen and Margalit, J. Biochem. 270:325-330, 1990). Certain albumin-porphyrin compounds have also been developed as anti-HIV agents, in which the porphyrin derivatives include hemin, proto-porphyrin, meso-porphyrin, iron meso-porphrin, hemato-porphyrin, iron hematoporphyrin, deutero-porphyrin copper chlorophyllin (International Publication No. WO 9303035 published Feb. 18, 1993).

Heme-HSA has never been shown to reversibly bind oxygen. The heme moiety is presumably not configured into the protein in such a way that it is shielded from the oxidation reaction that would occur if oxygen binds.

However, optimization of human serum albumin as an oxygen carrier is provided by the HSA-porphyrin compounds of the present invention, in which formation of a complex between HSA and a suitable oxygen-binding moiety produces a mobile oxygen carrier which reversibly binds oxygen and thus can be used as a blood substitute.

SUMMARY OF THE INVENTION

The invention is directed to compositions comprising human serum albumin-porphyrin (HSA-P) complexes, methods for their production, and the use of these molecules as blood substitutes. The various porphyrins provided by the invention can bind oxygen reversibly, and they can be used to transport and deliver oxygen when bound to an HSA carrier. The invention further provides HSA-P complexes which do not exhibit vasoactivity. The invention also provides various modified porphyrins, including picket-fence porphyrin, as the oxygen-binding moiety in the HSA-P complex.

The invention is illustrated by means of examples in which methods are given for the synthesis of HSA-P, and by examples in which the oxygen-carrying capacity of the HSA-P is demonstrated, and by an example in which the lack of vasoactivity of the HSA-P of the present invention is illustrated.

5. DETAILED DESCRIPTION OF THE INVENTION

The invention is directed to compositions comprising human serum albumin-porphyrin (HSA-P) complexes, methods for their production, and the use of these molecules as blood substitutes. The various porphyrins provided by the invention can bind oxygen reversibly, and they can be used to transport and deliver oxygen when bound to an HSA carrier. The invention further provides HSA-P complexes which do not exhibit vasoactivity. The invention also provides various modified porphyrins, including picket-fence porphyrin, as the oxygen-binding moiety in the HSA-P complex.

The invention is illustrated by means of examples in which methods are given for the synthesis of HSA-P complexes, and by examples in which the oxygen-carrying capacity of the HSA-P complexes is demonstrated, and by an example in which the lack of vasoactivity of the HSA-P complexes of the present invention is illustrated.

5.1 Preparation of MSA-P

The invention provides human serum albumin-porphyrin (HSA-P) complexes. These are hybrid molecules that complex HSA with an oxygen-binding moiety. These HSA-P complexes provide several advantages over the prior art. First, the biocompatibility of human serum albumin (which is already used as a plasma expander and resuscitation fluid) allows the HSA-P complex to readily transport to and access numerous tissues and organs. Secondly, in a HSA-P complex preferred for use, such HSA-P complex does not have the vasoconstrictive potential of hemoglobin, i.e., the HSA-P complex does not promote high blood pressure. It is shown herein that an HSA-P complex does not have the vasoconstrictive potential of hemoglobin (Example 10, infra), a side effect which can limit its clinical effectiveness.

Thus, in a preferred aspect, the invention provides for HSA-P complexes which are capable of reversible cycles of oxygenation and deoxygenation, and which does not exhibit significant vasoactivity.

HSA-P complexes of the present invention may be screened for oxygen binding by any method known in the art, e.g., tonometry (Riggs and Wolbach, J. Gen. Physiol. 39:585-605, 1956) (see Example 7, infra) in order to determine the degree of saturation of the porphyrin moiety as a function of the oxygen partial pressure. This data can be extrapolated to a Hill Plot which allows for an assessment of the cooperativity of oxygen binding.

HSA-P complexes of the present invention may be screened for reversibility of the oxygen binding by any method known in the art, e.g., spectrophotometrically by successive cycles of incubation with oxygen, followed by repeated vacuum evacuations with nitrogen purges (see Example 8, infra). Characteristic changes in absorption that indicate oxy- and deoxy- complexes at a particular wavelength may be used to determine the potential of an HSA-P for use as an oxygen carrier.

In a preferred embodiment, the porphyrin in the HSA-P complex is picket fence porphyrin (PFP). As described in Section 2 above, PFP is a modified heme. By virtue of its structure, this molecule can be used to provide an oxygen-binding moiety to an exogenous protein.

A HSA-P complex of the invention is that containing a PFP that is a compound of the following formula:

wherein
M is Co, Fe, or Mn;
$R^1$ is $C(CH_3)_3$ or $(CH_2)_n C_6 H_4 R^2$;
$R^2$ is H, CN, $NO_2$, CO-phenyl, halogen, $CF_3$, $NHCOR^3$, $CO_2R^3$, $OR^3$, $SO_2N(R^3)_2$, $NR^4R^5$, or $SO_2R^6$;
$R^3$ is H, $C_1$–$C_6$ alkyl or phenyl;
$R^4$ and $R^5$, independently are H or $C_1$–$C_4$ alkyl;
$R^6$ is $C_1$–$C_6$ alkyl or phenyl; and
n is 0–8.

The invention provides various picket fence porphyrins that retain an oxygen binding capacity and are capable of binding the human serum albumin and serving as a mobile oxygen carrier.

Human serum albumin may be prepared by any method known in the art such as purification from a natural source (including purification by polyacrylamide gel electrophoresis, immunoprecipitation or affinity chromatography), chemical synthesis, and recombinant DNA technology. The technique of Cohn involving successive cycles of precipitation from plasma to yield the 98% pure Fraction V albumin may be employed (Cohn et al., J. Am. Chem. Soc. 68:459-475, 1946). Recombinant DNA techniques may be used with the cloned gene (Hawkins and Dugaiczyk, Gene 19: 55-58, 1982) to express the recombinant protein in bacteria or any of other known expression systems in the art (see Current Protocols in Molecular Biology, Ausubel, F., et al., eds., Wiley and Sons, 1987). Alternatively, the protein may be purchased from known suppliers including Cutter Laboratories (Dallas, Texas), Abbott Laboratories (North Chicago, Ill.), and Sigma Chemical Company (St. Louis, Mo.).

The porphyrins in the HSA-P complexes of the instant invention may be made by methods previously described (Collman et al., J. Am. Chem. Soc. 97:1427-1439, 1975). Condensation of the appropriately substituted nitrobenzaldehyde with pyrrole yields a tetra-(nitrophenyl)porphyrin. Reduction of the nitro group using excess tin chloride in concentrated mineral acid yields the corresponding amine. Condensation of the tetra-amine with the appropriate acid chloride affords the substituted porphyrins of the instant invention. The requisite acid chlorides are either commercially available (Aldrich Chemical Co.) or can be made by standard methods from the corresponding carboxylic acids and thionyl chloride. Standard protecting groups may be necessary to prepare some of the requisite acid chlorides. Removal of the protecting groups can be affected under standard conditions following condensation of the amine with acid chloride.

HSA-P complexes derivatives may be prepared by reacting a porphyrin, in a specific embodiment a picket-fence porphyrin, with carbon monoxide (CO) to form CO-PFP. This complex is then further reduced with dithionite. The CO-PFP is then mixed with HSA, and formation of a complex with HSA can be assessed by chomatography and ultrafiltration. Removal of the CO is accomplished by illumination of the sample with light in a tonometer with oxygen, yielding an $O_2$-HSA-PFP complex. The oxygen can be removed with nitrogen, leaving the HSA-PFP complex.

The invention also provides for HSA-P complexes in which the HSA is in the form of multimers, which in a preferred embodiment may be a dimer formed by the creation of a disulfide bond between HSA monomers, and which may prevent extravasation of the HSA-P from the circulation. Such dimers can be formed by the addition of mercuric chloride to a solution of HSA monomers, which causes the thiol-containing albumin to dimerize through a mercury bridge (Hughes and Dintzis, J. Biol. Chem. 239:845-849, 1964). Subsequent oxidation of this HSA dimer by treatment with iodine results in a formation of a disulfide bond between the cysteines to form a disulfide dimer (Straessle, J. Am. Chem. Soc. 76:3138-3142, 1954). HSA disulfide dimers may also be prepared by oxidation of HSA monomers with ferricyanide (Andersson, Biochem. et Biophys. Acta 117:115-133, 1966) or by oxidation at alkaline pH in the presence of oxygen. HSA multimers of the instant invention can also be prepared by crosslinking with any of known reagents in the art, including carbodiimide and glutaraldehyde.

HSA-P complexes of the present invention may be screened for oxygen binding by any method known in the art, e.g., tonometry (Riggs and Wolbach, J. Gen. Physiol. 39:585-605, 1956) (see Example 7, infra) in order to determine the degree of saturation of the porphyrin moiety as a function of the oxygen partial pressure. This data can be extrapolated to a Hill Plot which allows for an assessment of the cooperativity of oxygen binding.

HSA-porphyrins of the present invention may be screened for reversibility of the oxygen binding by any method known in the art, e.g., spectrophotometrically by successive-cycles of incubation with oxygen, followed by repeated vacuum evacuations with nitrogen purges (see Example 8, infra). Characteristic changes in absorption that indicate oxy- and deoxy- complexes at a particular wavelength may be used to determine the potential of an HSA-P complex for use as an oxygen carrier.

HSA-porphyrins of the present invention may be screened for vasoactivity by any method known to those skilled in the art, including but not limited to the use of in vitro models such as the phenylephrine-evoked contraction of endothelium (See Example 10, infra).

5.2. Utilities of the Invention

The HSA-P compositions of the present invention may be used as blood substitutes or as a blood plasma expander, in a pharmaceutical composition with an acceptable carrier, and with other plasma expanders, or in any application where a physiological oxygen carrier is needed. The pharmaceutical carriers may be such physiologically compatible buffers as Hank's or Ringer's solution, physiological saline, a mixture consisting of saline and glucose, and heparinized sodium-citrate-citrate acid-dextrose solution. The HSA-P complexes produced by the methods of the present invention can be mixed with colloidal-like plasma substitutes and plasma expanders such as linear polysaccharides (e.g., dextran), hydroxyethyl starch, balanced fluid gelatin, and other plasma proteins. Additionally, the HSA-PFP may be mixed with water soluble, physiologically acceptable, polymeric plasma substitutes, examples of which include polyvinyl alcohol, poly (ethylene oxide), polyvinylpyrrolidone, and ethylene oxide-polypropylene glycol condensates. Techniques and formulations for administering the compositions comprising the HSA-P complexes generally may be found in Remington's Pharmaceutical Sciences, Meade Publishing Co., Easton, Pa., latest edition.

Pharmaceutical compositions for use in accordance with the present invention may be formulated in conventional manner using one or more physiologically acceptable carriers or excipients.

The compounds may be formulated for administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Toxicity and therapeutic efficacy of such compounds can be determined by standard pharmaceutical procedures in cell cultures or experimental animals, e.g, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred.

The data obtained from animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms). Such information can be used to more accurately determine useful doses in humans.

Subjects for treatment with the compounds of the present invention include humans and other mammals such as monkeys, chimpanzees, rodents, pigs, cows, horses, dogs, cats, and particularly primates.

6. EXAMPLE: PREPARATION OF HUMAN-SERUM ALBUMIN-PICKET FENCE PORPHYRINS

Figure 1:
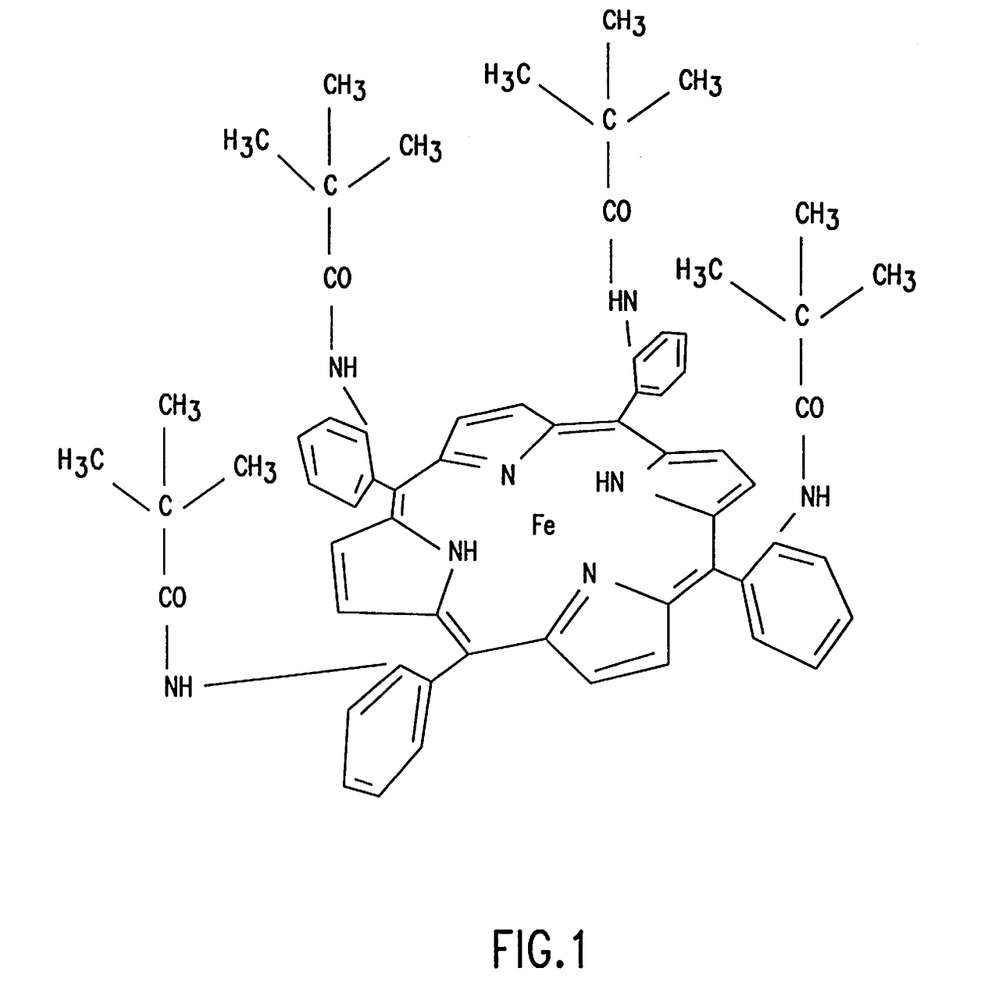
FIG. 1. Structure of picket fence porphyrin #1: Fe meso-tetra (a, a, a,a-pivalamido-phenyl) porphine.
Figure 2:
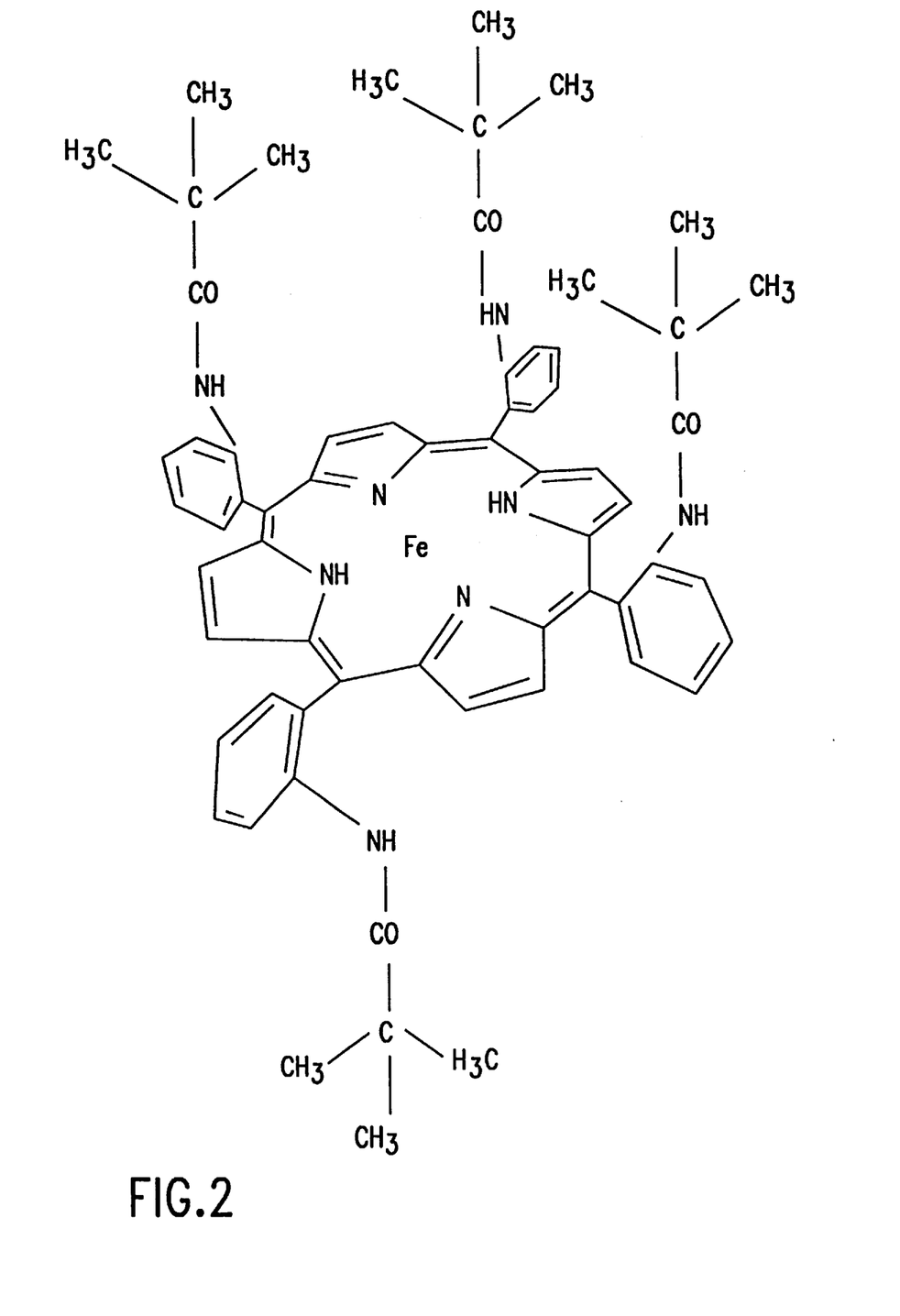
FIG. 2. Structure of picket fence porphyrin #2: Fe meso-tetra (a,a,a,o-pivalamido-phenyl) porphine.

A 500 $\mu$M stock solution of Fe meso-tetra (a,a,a,a-pivalamido-phenyl) porphine (PFP #1) (FIG. 1) or Fe meso-tetra (a,a,a,o-pivalamido-phenyl) porphine (PFP#2) (FIG. 2) (both purchased from Porphyrin Products, Provo, Utah) was prepared in 100% dimethyl sulfoxide (DMSO) containing 1 mM N-methylimidazole.

Figure 3:
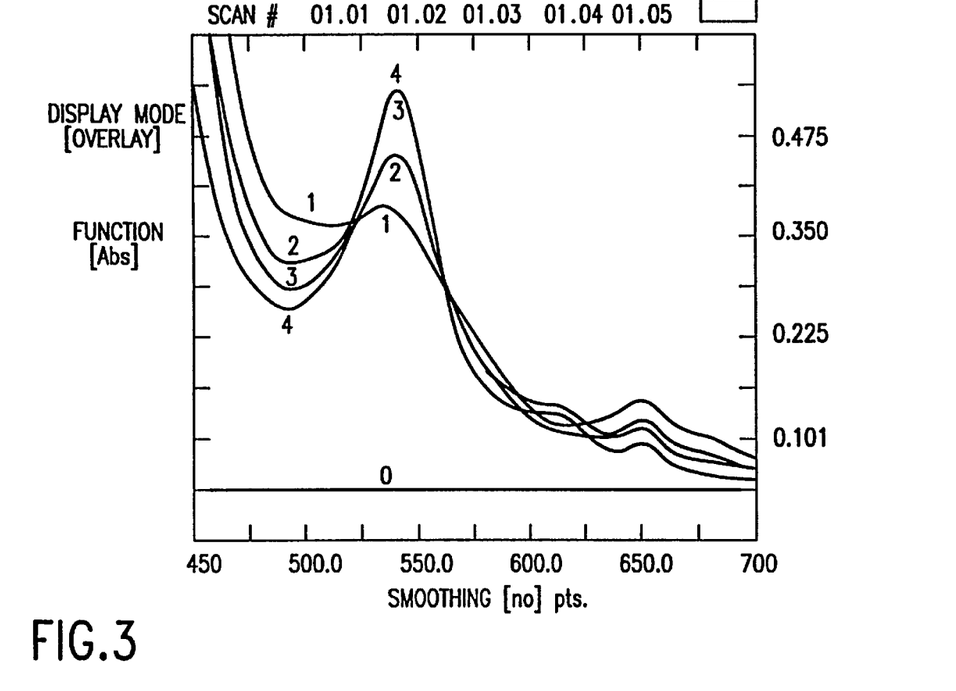
FIG. 3. Absorption spectra of HSA-PFP #1 in the wavelength region from 450 to 700 nm. Optical pathlength was 1 cm. The solvent was DMSO made 1 Mm in M-methylimidazole. The nominal concentration of #1 was 55 $\mu$M.
Figure 4:
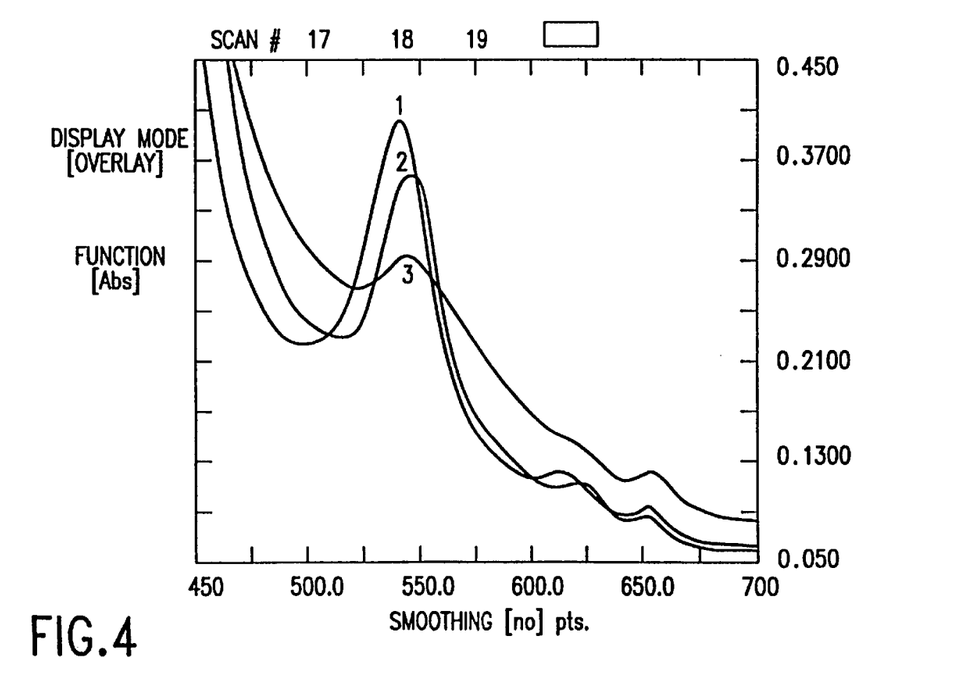
FIG. 4. Absorption spectra of the various forms of the HSA-PFP #1 with human serum albumin. Curve 1 corresponds to the carbon monoxide derivative; curve 2 to the oxygenated derivative and curve 3, the deoxygenated derivative. The pathlength was 1 cm.

The spectrum of this material (60 μM) (PFP#2) after degassing, is shown in FIG. 3, spectrum 1. Addition of carbon monoxide (CO) results in spectrum 2, indicating that the PFP is partially reduced ($Fe^{2+}$). Addition of dithionite further reduces the PFP (spectrum 3). The CO-PFP was mixed with HSA (Albumin-USP 25%; Cutter Pharmaceuticals, Dallas, Tex.) in 50 mM Bis-Tris pH 7 (3 ml PFP (60 μM) with 7.5 ml HSA (14.5 μM); measured PFP/HSA ratio (Fe/protein) was 0.9. The spectrum of the mixture is still indicative of CO-PFP. The mixture was concentrated on an Amicon, PM-30 membrane (no color in filtrate) and then passed through a Sephadex G-25 column. The spectrum of the fractions that contain HSA is shown in FIG. 4, spectrum 1. It is evident that a CO-PFP-HSA complex has formed and that the complex is stable (i.e., remains in the reduced state in aqueous solution). Removal of CO through illumination of the sample with bright light, in a tonometer filled with oxygen, results in a $O_2$-PFP-HSA complex (spectrum 2). The oxygen can be removed by nitrogen (spectrum 3). The S PFP/HSA ratio after Sephadex was 0.65.

7. EXAMPLE: ABSORPTION SPECTRA OF OXYGEN BINDING BY THE HSA-PFP COMPLEX #1

A 5 μM PFP-CO/HSA complex was prepared in 50 mM Bis-Tris pH 7.0. This solution was then pipetted into a tonometer, treated with $N_2$, and rotated in a water bath at 25° C. for 10 minutes under a lamp to allow for equilibration. This was followed by the addition of 1 ml of $O_2$ (5.75 μM) and subsequent equilibration for 5 minutes as above except in the absence of the lamp. The oxygen titrations were monitored spectrophotometrically and resulted in FIG. 5.

Figure 5:
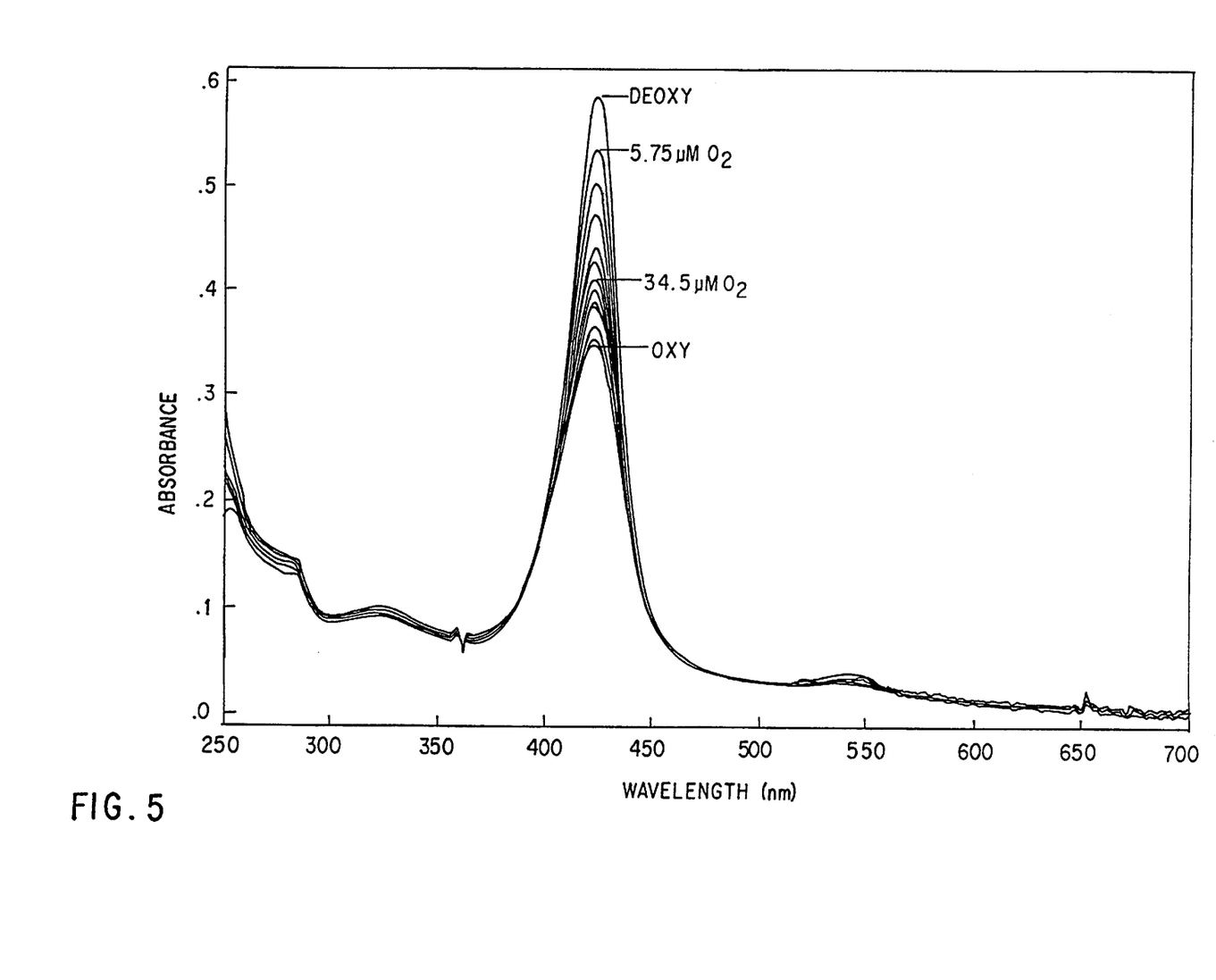
FIG. 5. Absorption spectra showing the raw data from an oxygen equilibrium experiment with 5 $\mu$M HSA-PFP #1 complex. The complex was in 50 Mm Bis-Tris, pH 7.0 at 20° C. The deoxygenated derivative has the highest molar absorptivity at 422 nm and the oxygenated derivative has the lowest absorptivity at 422 nm. Each intermediate spectrum corresponds to the partially oxygenated derivative at different oxygen concentrations.

The family of curves shown in FIG. 5 show varying degrees of saturation of HSA-PFP #1 as a function of oxygen concentration. Although the shape and position of the absorption peaks differ from those of hemoglobin, the family of spectra seen in FIG. 5 are qualitatively the same as one would see in an oxygen equilibrium experiment done with hemoglobin.

8. EXAMPLE: OXYGEN BINDING OF HSA-PFP #1

Figure 6:
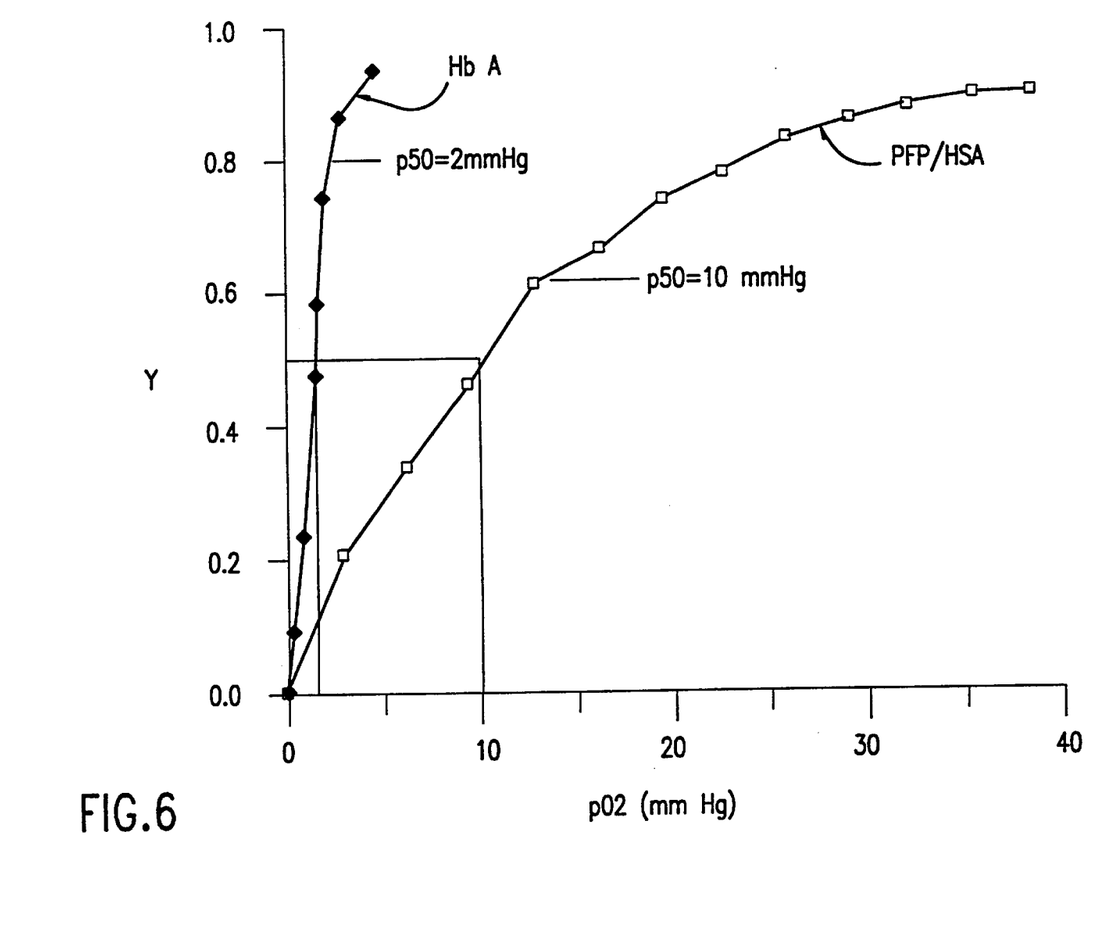
FIG. 6. The percent oxygen saturation of human hemoglobin A and HSA-PFP #1 as a function of oxygen concentration (pO$_2$ in mm Hg) is shown. —□—HSA-PFP#1; —◆—: hemoglobin A.
Figure 7:
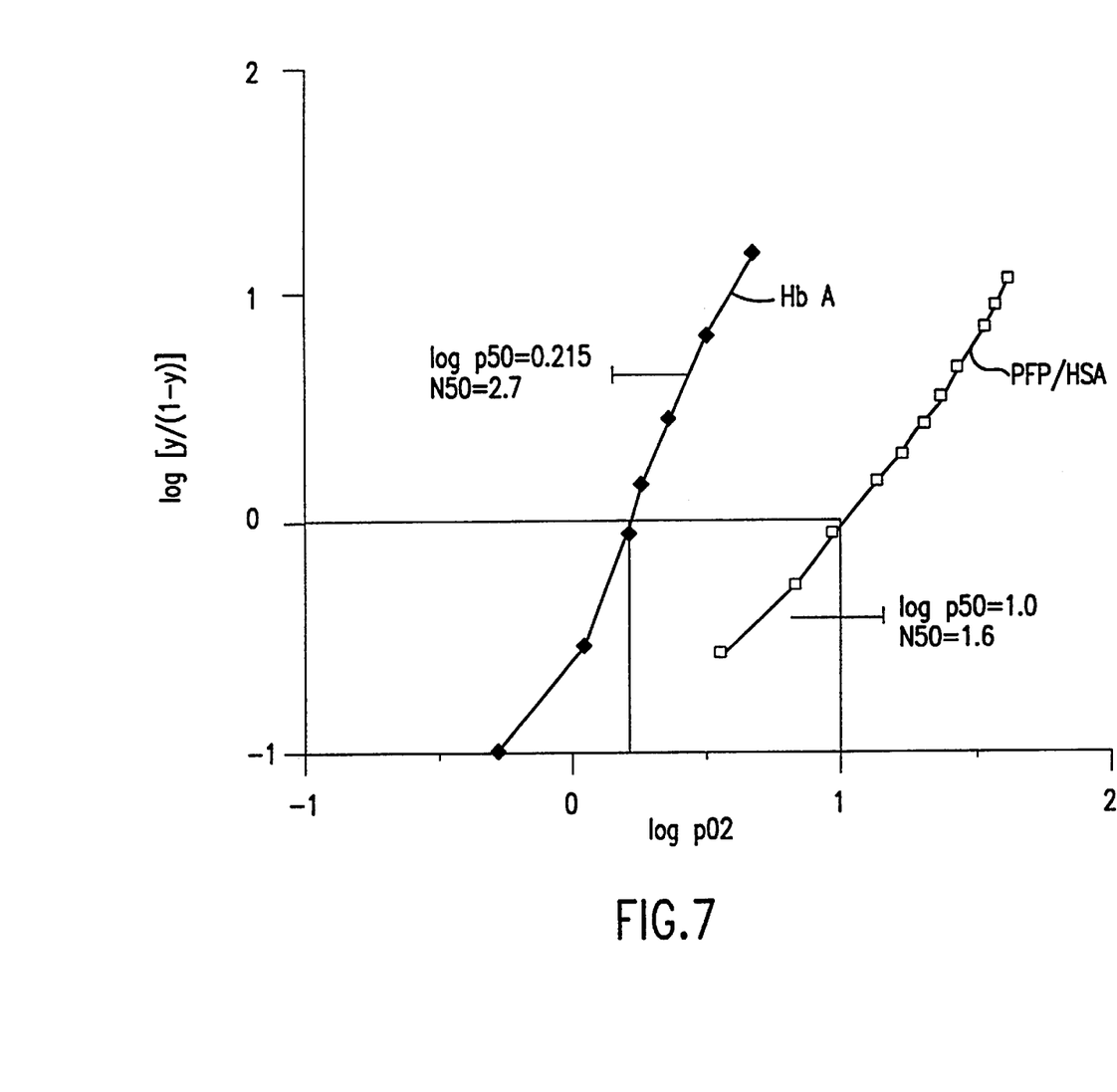
FIG. 7. Hill plots for 5 mM HSA-PFP #1 and human hemoglobin A in 50 mM Bis-Tris, pH 7.0 at 20° C. using data derived from FIG. 6. —□— HSA-PFP#l; —◆—: hemoglobin A.
Figure 8A:
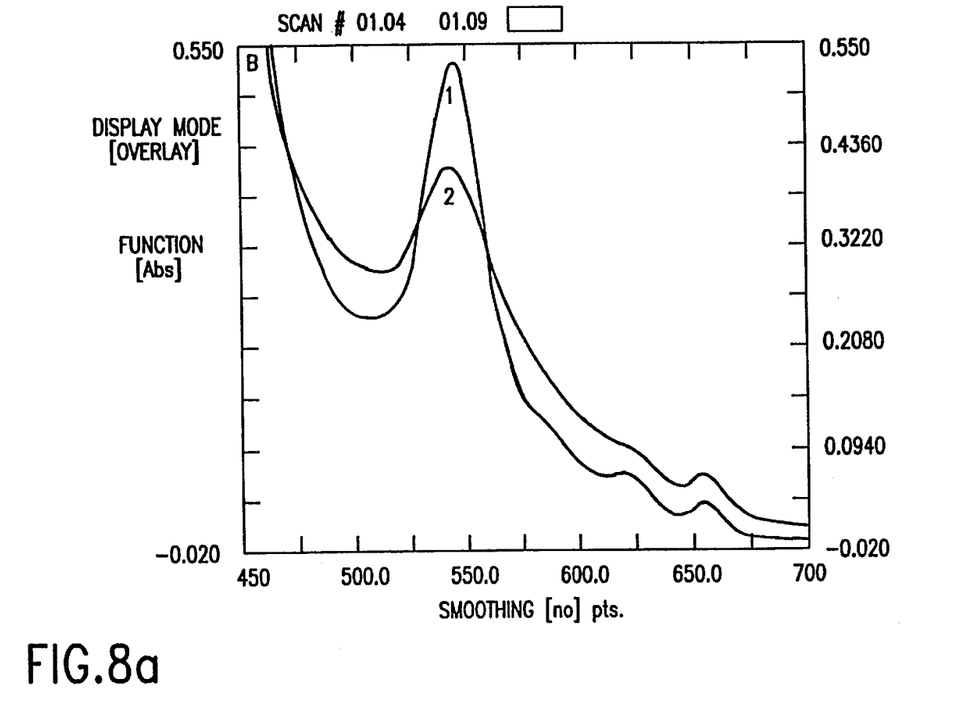
FIGS. 8a–d Absorption spectra of HSA-PFP #2 cycling between the oxygenated (O$_2$) (1) and deoxygenated (N$_2$) (2) derivatives.
Figure 8B:
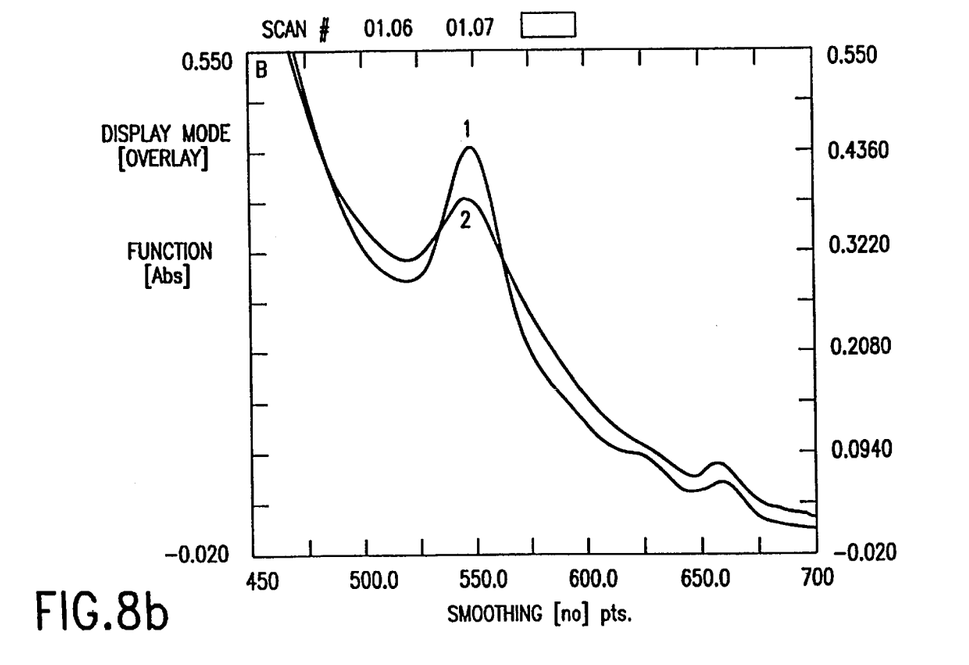
Figure 8C:
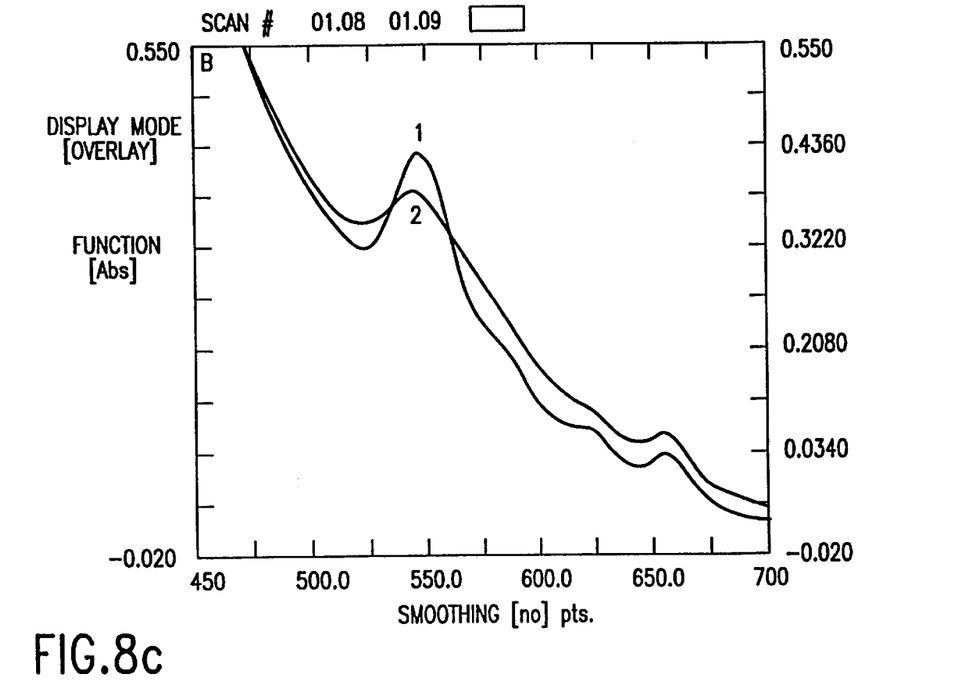
Figure 8D:
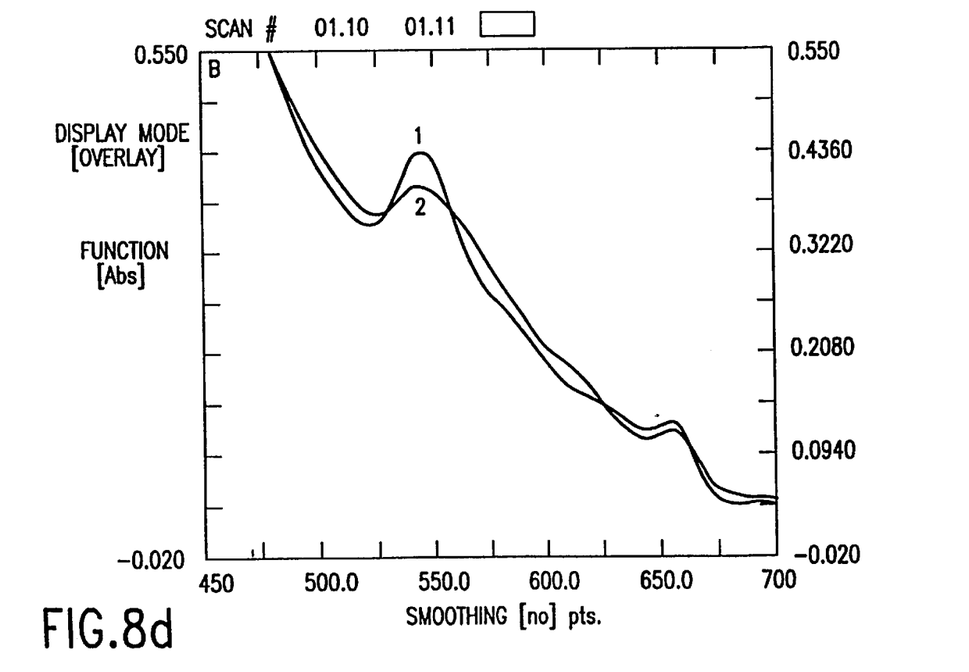

The $P_{50}$ for HSA-PFP #1 and human Hemoglobin A (HbA) were determined by tonometry (Riggs and Wolbach, 1956, J. Gen. Physiol. 39:585-60.5). Specifically, a HSA-PFP solution was placed in a gas-tight vessel which has an attached spectrophotometer cell. The solution was deoxygenated by a series of repeated vacuum evacuations followed by nitrogen purges. After the deoxygenated state was obtained, a "deoxy" spectrum was obtained. Next, a series of metered oxygen additions were made with a spectrum taken after each addition yielding a set of curves from which can be calculated (using established extinction coefficients) the degree of saturation of the heme sites with oxygen as a function of the oxygen partial pressure (FIG. 6). The percent oxygen saturation of human HbA and HSA-PFP #11 as a function of oxygen concentration is shown. The oxygen affinity ($P_{50}$) of HbA is high (2 mm Hg) relative to that of HSA-PFP #1 (10 mm Hg). This data is transformed into the Hill plot shown in FIG. 7. The degree of cooperativity of HbA is high (n50=2.7) relative to that of HSA-PFP #1 n50=1.6).

9. EXAMPLE: OXYGENATION CYCLES FOR HSA-PFP #2

HSA-PFP #2 was deoxygenated in a tonometer as described in Example 7. A deoxy spectrum was obtained. The oxygenated form of the molecule was obtained by adding pure $O_2$ to the tonometer. The oxygen spectrum was obtained.

FIG. 8 (a–d) show four successive cycles of deoxygenation/oxygenation. The decrease in the difference spectra for 8(a–d) can be attributed to autoxidation of the $Fe^{2+}$ to $Fe^{3+}$ in the HSA-PFP #2 complex. The $Fe^{3+}$ derivative cannot bind oxygen.

10. EXAMPLE: VASOACTIVITY EXPERIMENT FOR HSA-PFP #1

Male Wistar rats (300–400 g) were euthanized by intraperitoneal injection of sodium pentobarbitol (50 mg/kg). The thoracic aortas were excised and stored in cold modified Krebs-Ringer solution containing NaCl 118.3 mM, KCl 4.7 mM, $MgSO_4$ 1.2 mM, $KH_2PO_4$ 1.2 mM, $CaCl_2$ 2.5 mM, $NaHCO_3$ 25 mM, Ca EDTA 16 μM, and glucose 11.1 mM (control solution). Arteries were cleared of fat and connective tissue and cut into rings. For some experiments the endothelium was removed mechanically by placing rings on filter paper wetted with the control solution, inserting the tip of a forceps into the lumen, and rolling the ring back and forth on the filter paper. The presence of the endothelium was confirmed by determining the relaxation to acetylcholine ($10^{-6}$M) in arteries contracted with phenylephrine ($10^{-6}$M). The rings were placed in 24-well multiwell plates with Dulbecco's Modified Eagle's Medium and Ham's F-12 Medium (DMEM/F12) (1 ml), in the presence or absence of endotoxin (LPS) 200 ng/ml, for 4 hours. After incubation, the rings were suspended in organ chambers containing 10 ml of control solution (37° C., pH 7.4) and aerated with 95% $O_2$ and 5% $CO_2$. Rings were stretched progressively to 2.5 to 3 g of tension. Changes in isometric tension were recorded with a force transducer connected to an analog-to-digital input board (Scientific Solutions, Inc., Solon, Ohio) in an IBM 386/30 mHz personal computer. The aortic rings were rinsed three times with warm control solution, rested for 30 minutes, and the incubated with bovine cell-free Hgb, Heme-HSA, or HSA-PFP for 5 minutes before a concentration-contraction curve to phenylephrine ($10^{-9}$ to $10^{-5}$M) was obtained.

Figure 9:
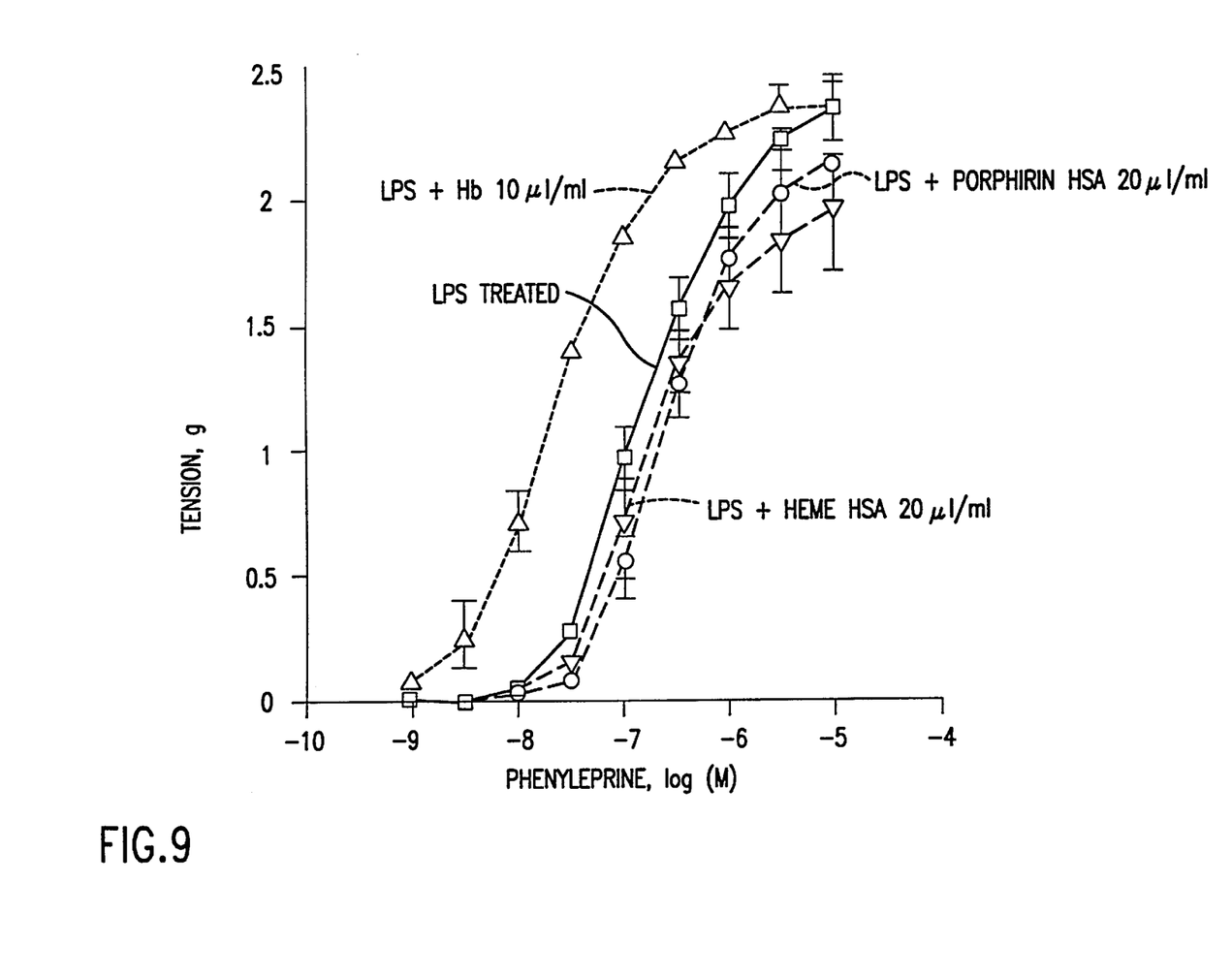
FIG. 9. Effects of bovine cell-free hemoglobin (Hgb), picket-fence porphyrin human serum albumin (HSA-PFP) (#1) and heme-HSA in the concentration-contraction curves evoked by phenylephrine in rat aorta ring with endothelium, incubated for 4 hours in culture medium containing endotoxin (LPS), 200 ng/ml. Results are presented as mean +/− SEM of 4 different experiments. —□—: LPS treated; —Δ—: LPS+10$\mu$l/ml hemoglobin; —o— LPS+20 $\mu$l/ml HSA-PFP#2; —∇—: LPS +20 $\mu$l/ml HSA-heme.

FIG. 9 shows that the HSA-PFP #1 at 5 mg/ml had no significant effect on phenylephrine-evoked contraction of rat aortic rings treated with endotoxin.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Various publications are cited herein, the disclosures of which are incorporated by reference in their entireties.

What is claimed is:

1. A complex of human serum albumin and a picket fence porphyrin, which reversibly binds oxygen.

2. The complex of claim 1 which is purified.

3. The complex of claim 1 in which the picket fence porphyrin is ferrous meso-tetra (a,a,a,a-pivalamidophenyl) porphyrin.

4. A pharmaceutical composition for use as a blood substitute or blood plasma expander comprising a amount of the complex of claim 3 effective for use as a blood substitute or blood plasma expander; and a pharmaceutically acceptable carrier.

5. A method for replacing or increasing the circulatory blood volume or increasing oxygen delivery to tissues in a mammal comprising administering to said mammal an amount of the complex of claim 3 effective to replace or increase the circulatory blood volume or increase oxygen delivery to tissues.

6. The complex of claim 1 in which the picket fence porphyrin is ferrous meso-tetra (a,a,a,o-pivalamidophenyl) porphyrin.

7. A pharmaceutical composition for use as a blood substitute or blood plasma expander comprising an amount of the complex of claim 6 effective for use as a blood substitute or blood plasma expander; and a pharmaceutically acceptable carrier.

8. A method for replacing or increasing the circulatory blood volume or increasing oxygen delivery to tissues in a mammal comprising administering to said mammal an amount of the complex of claim 6 effective to replace or increase the circulatory blood volume or increase oxygen delivery to tissues.

9. The complex of claim 1 in which the picket-fence porphyrin is wherein
M is Co, Fe, or Mn;
$R^1$ is $C(CH_3)_3$, or $(CH_2)_nC_6H_4R^2$;
$R^2$ is H, CN, $NO_2$, CO-phenyl, halogen, $CF_3$, $NHCOR^3$, $CO_2R^3$, $OR^3$, $SO_2N(R^3)_2$, $NR^4R^5$, or $SO_2R^6$;
$R^3$ is H, $C_1$–$C_6$ alkyl or phenyl;
$R^4$ and $R^5$, independently are H or $C_1$–$C_4$ alkyl;
$R^6$ is $C_1$–$C_6$ alkyl or phenyl; and
n is 0–8.

10. A pharmaceutical composition for use as a blood substitute or blood plasma expander comprising an amount of the complex of claim 9 effective for use as a blood substitute or blood plasma expander; and a pharmaceutically acceptable carrier.

11. A method for replacing or increasing the circulatory blood volume or increasing oxygen delivery to tissues in a mammal comprising administering to said mammal an amount of the complex of claim 9 effective to replace or increase the circulatory blood volume or increase oxygen delivery to tissues.

12. A pharmaceutical composition for use as a blood substitute or blood plasma expander comprising an amount of the complex of claim 1 effective for use as a blood substitute or blood plasma expander; and a pharmaceutically acceptable carrier.

13. The composition of claim 12 in which the complex is purified.

14. A method for replacing or increasing the circulatory blood volume or increasing oxygen delivery to tissues in a mammal comprising administering to said mammal an amount of the complex of claim 1 effective to replace or increase the circulatory blood volume or increase oxygen delivery to tissues.

15. The method of claim 14 in which the complex is purified.

16. A pharmaceutical composition for use as a blood substitute comprising an amount of a complex of human serum albumin and porphyrin effective for use as a blood substitute, which complex reversibly binds oxygen; and a pharmaceutically acceptable carrier.

17. A pharmaceutical composition for use as a blood substitute comprising an amount of a complex of human serum albumin and porphyrin effective for use as a blood substitute, which complex reversibly binds oxygen, and is substantially not vasoactive, as detected in an in vitro assay; and a pharmaceutically acceptable carrier.

18. A method for replacing or increasing the circulatory blood volume or increasing oxygen delivery to tissues in a mammal comprising administering to said mammal an amount of a complex of human serum albumin and porphyrin effective to replace or increase the circulatory blood volume or increase oxygen delivery to tissues, which complex reversibly binds oxygen.

19. A method for replacing or increasing the circulatory blood volume or increasing oxygen delivery to tissues in a mammal comprising administering to said mammal an amount of a complex of human serum albumin and porphyrin effective to replace or increase the circulatory blood volume or increase oxygen delivery to tissues, which complex reversibly binds oxygen and is substantially not vasoactive, as detected in an in vitro assay.

20. A method for producing a complex of human serum albumin and a picket fence porphyrin which reversibly binds oxygen comprising:
(a) mixing a picket fence porphyrin with carbon monoxide (hereinafter CO) to form a CO-picket fence porphyrin complex;
(b) reacting the CO-picket fence porphyrin complex with human serum albumin to yield a CO-picket fence porphyrin-human serum albumin complex;
(c) removing the CO from the CO-picket fence porphyrin-human serum albumin complex of step (b) by illumination of the complex in a tonometer filled with oxygen;
(d) removing the oxygen with a nitrogen purge; and
(e) recovering the human serum albumin-picket fence porphyrin complex, wherein the human serum albumin-picket fence porphyrin complex reversibly binds oxygen.

21. A method for producing a complex of human serum albumin and porphyrin which reversibly binds oxygen, comprising incubating a picket-fence porphyrin with human serum albumin under conditions such that a complex of picket-fence porphyrin and human serum albumin forms.

22. A complex of human serum albumin and a capped porphyrin, which reversibly binds oxygen.

23. The complex of claim 22 which is purified.

24. A pharmaceutical composition for use as a blood substitute or blood plasma expander comprising an amount of the complex of claim 22 effective for use as a blood substitute or blood plasma expander; and a pharmaceutically acceptable carrier.

25. The composition of claim 24 in which the complex is purified.

26. A method for replacing or increasing the circulatory blood volume or increasing oxygen delivery to tissues in a mammal comprising administering to said mammal an amount of the complex of claim 22 effective to replace or increase the circulatory blood volume or increase oxygen delivery to tissues.

27. The method of claim 26 in which the complex is purified.

28. A complex of human serum albumin and a basket handle porphyrin which reversibly binds oxygen.

29. The complex of claim 28 which is purified.

30. A pharmaceutical composition for use as a blood substitute or blood plasma expander comprising an amount of the complex of claim 28 effective for use as a blood substitute or blood plasma expander; and a pharmaceutically acceptable carrier.

31. The composition of claim 30 if which the complex is purified.

32. A method for replacing or increasing the circulatory blood volume or increasing oxygen delivery to tissues in a mammal comprising administering to said mammal an amount of the complex of claim 28 effective to replace or increase the circulatory blood volume or increase oxygen delivery to tissues.

33. The method of claim 32 in which the complex is purified.

34. A method for producing a complex of human serum albumin and a capped porphyrin which reversibly binds oxygen comprising:

(a) mixing a capped porphyrin with carbon monoxide (hereinafter CO) to form a CO-capped porphyrin complex; (b) reacting the CO-capped porphyrin complex with human serum albumin to yield a CO-capped porphyrin-human serum albumin complex;

(c) removing the CO from the CO-capped porphyrin-human serum albumin complex of step (b) by illumination of the complex in a tonometer filled with oxygen;

(d) removing the oxygen with a nitrogen purge; and (e) recovering the human serum albumin-capped porphyrin complex, wherein the human serum albumin-capped porphyrin complex reversibly binds oxygen.

35. A method for producing a complex of human serum albumin and porphyrin which reversibly binds oxygen, comprising incubating a capped porphyrin with human serum albumin under conditions such that a complex of capped porphyrin and human serum albumin forms.

36. A method for producing a complex of human serum albumin and a basket handle porphyrin which reversibly binds oxygen comprising:

(a) mixing a basket handle porphyrin with carbon monoxide (hereinafter CO) to form a CO-basket handle porphyrin complex.

(b) reacting the CO-basket handle porphyrin complex with human serum albumin to yield a CO-basket handle porphyrin-human serum albumin complex;

(c) removing the CO from the CO-basket handle porphyrin-human serum albumin complex of step (b) by illumination of the complex in a tonometer filled with oxygen;

(d) removing the oxygen with a nitrogen purge; and (e) recovering the human serum albumin-basket handle porphyrin complex, wherein the human serum albumin-basket handle porphyrin complex reversibly binds oxygen.

37. A method for producing a complex of human serum albumin and porphyrin which reversibly binds oxygen, comprising incubating a basket handle porphyrin with human serum albumin under conditions such that a complex of basket handle porphyrin and human serum albumin forms.

38. A complex of human serum albumin and porphyrin, which reversibly binds oxygen.

39. The complex of claim 38 which is substantially not vasoactive, as detected in an in vitro assay.

40. The complex of claim 39 for which is purified.

41. A method for producing a complex of human serum albumin and porphyrin which reversibly binds oxygen, comprising:

a) mixing a porphyrin compound with CO to form a CO-porphyrin complex;

b) reacting the CO-porphyrin complex with human serum albumin to yield the CO-porphyrin-human serum albumin complex;

c) removing the CO by illumination of the complex in a tonometer filled with oxygen;

d) removing the oxygen with a nitrogen purge; and e) recovering the human serum albumin-porphyrin complex.

42. A method for producing a complex of human serum albumin and porphyrin which reversibly binds oxygen, comprising incubating a porphyrin that reversibly binds oxygen with human serum albumin under conditions such that a complex of porphyrin and human serum albumin forms that reversibly binds oxygen.

* * * * *